United States Patent
Lee et al.

(10) Patent No.: US 9,089,687 B2
(45) Date of Patent: Jul. 28, 2015

(54) DEVICE AND MEANS FOR ADJUSTING THE POSITION OF DBS BRAIN AND OTHER NEURAL AND MUSCULAR IMPLANTS

(71) Applicants: Chong Il Lee, Stanton, CA (US); Sergio Lara Pereira Monteiro, Los Angeles, CA (US)

(72) Inventors: Chong Il Lee, Stanton, CA (US); Sergio Lara Pereira Monteiro, Los Angeles, CA (US)

( * ) Notice: Subject to any disclaimer, the term of this patent is extended or adjusted under 35 U.S.C. 154(b) by 0 days.

(21) Appl. No.: 14/150,767

(22) Filed: Jan. 9, 2014

(65) Prior Publication Data
US 2014/0222018 A1    Aug. 7, 2014

Related U.S. Application Data

(62) Division of application No. 13/117,132, filed on May 26, 2011, now Pat. No. 8,670,837.

(60) Provisional application No. 61/396,334, filed on May 26, 2010.

(51) Int. Cl.
| | |
|---|---|
| *A61N 1/04* | (2006.01) |
| *A61N 1/05* | (2006.01) |
| *A61N 1/36* | (2006.01) |
| *A61N 1/368* | (2006.01) |
| *A61N 1/375* | (2006.01) |

(52) U.S. Cl.
CPC ............... *A61N 1/05* (2013.01); *A61N 1/0534* (2013.01); *A61N 1/0539* (2013.01); *A61N 1/3686* (2013.01); *A61N 1/36182* (2013.01); *A61N 1/36185* (2013.01); *A61N 1/057* (2013.01); *A61N 1/3684* (2013.01); *A61N 1/375* (2013.01)

(58) Field of Classification Search
None
See application file for complete search history.

(56) References Cited

U.S. PATENT DOCUMENTS

| | | | | |
|---|---|---|---|---|
| 6,416,520 | B1 * | 7/2002 | Kynast et al. | 606/130 |
| 8,340,783 | B2 * | 12/2012 | Sommer et al. | 607/116 |
| 2002/0183817 | A1 * | 12/2002 | Van Venrooij et al. | 607/116 |
| 2005/0267347 | A1 * | 12/2005 | Oster | 600/378 |
| 2006/0149336 | A1 * | 7/2006 | Meadows | 607/45 |
| 2006/0190054 | A1 * | 8/2006 | Malinowski et al. | 607/45 |
| 2008/0103572 | A1 * | 5/2008 | Gerber | 607/116 |

* cited by examiner

*Primary Examiner* — Brian T Gedeon

(57) ABSTRACT

A device, method and means to adjust the position of a picafina Deep Brain Stimulator (DBS). It is notoriously difficult to find the correct positioning of the picafina for best stimulating results, because it is not possible for the neurosurgeon to visually observe its position. We disclose a device, method and means to adjust the position of the picafina after it is inserted in the brain, for the best stimulating effect.

15 Claims, 16 Drawing Sheets

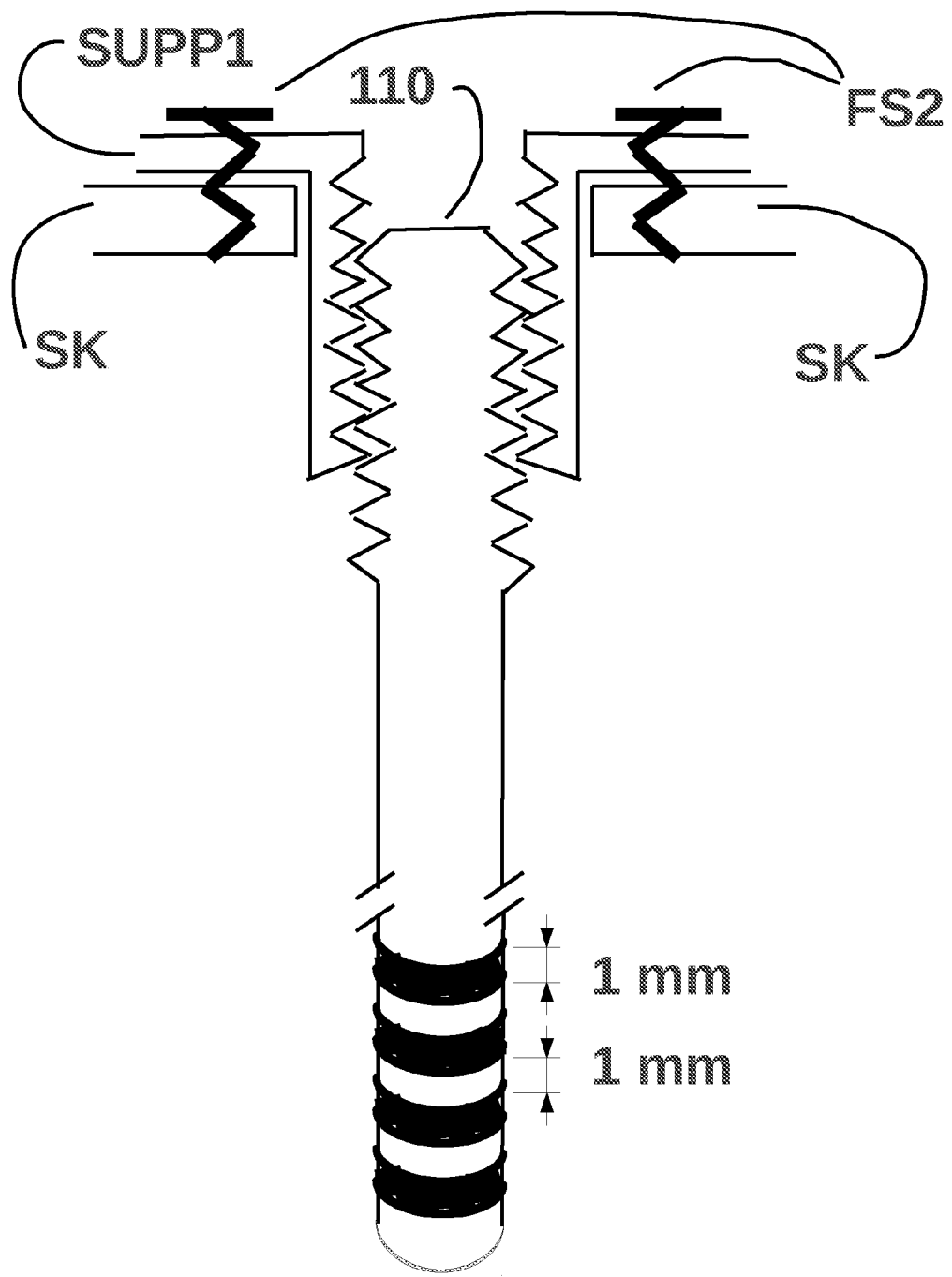

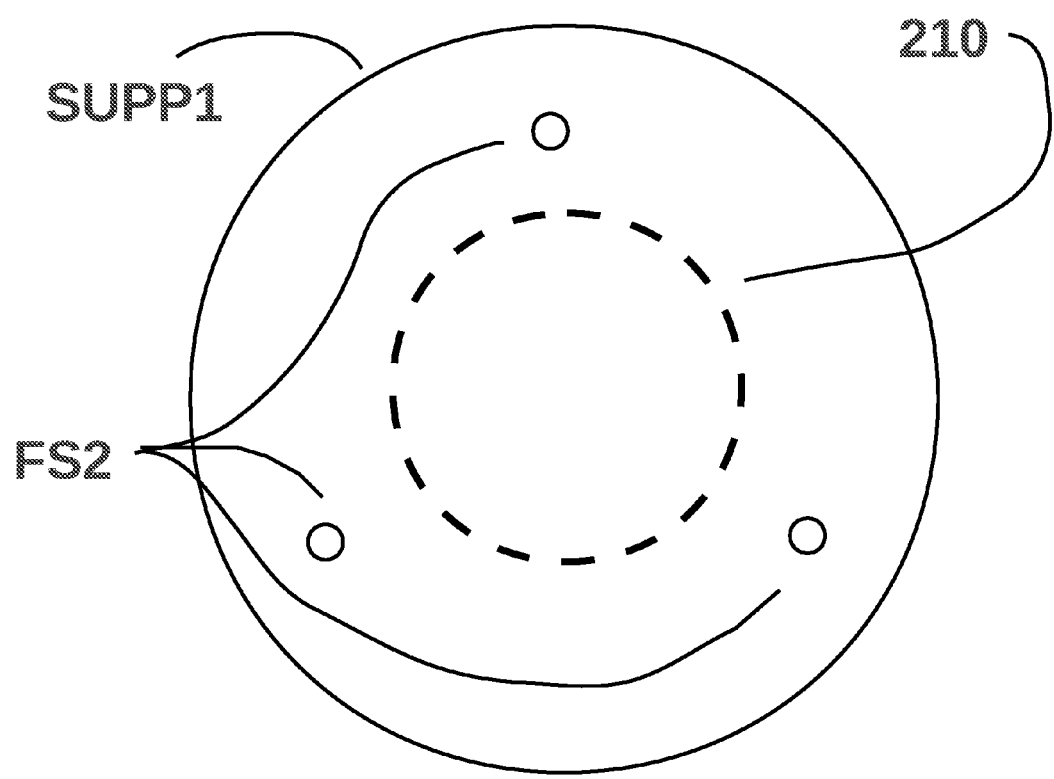

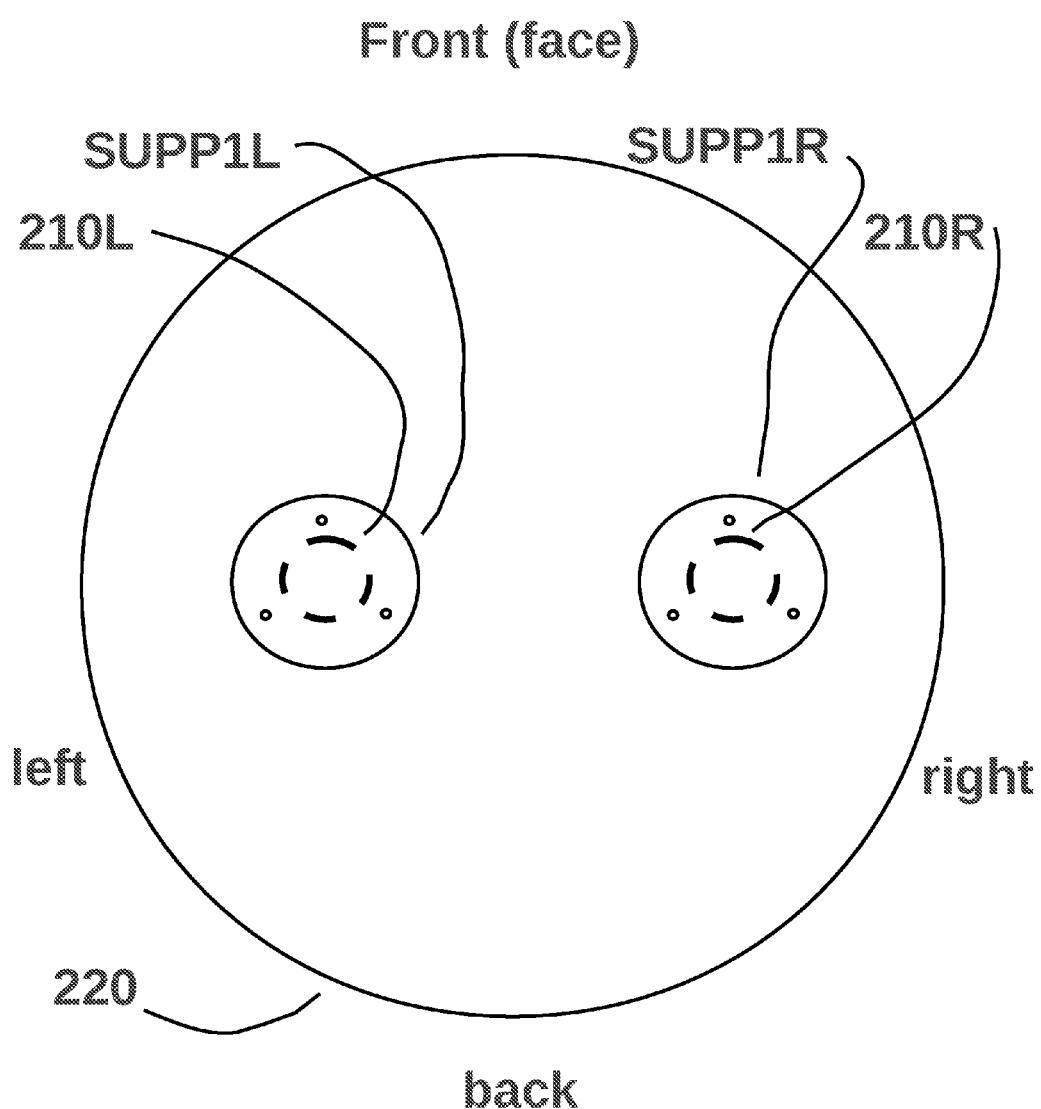

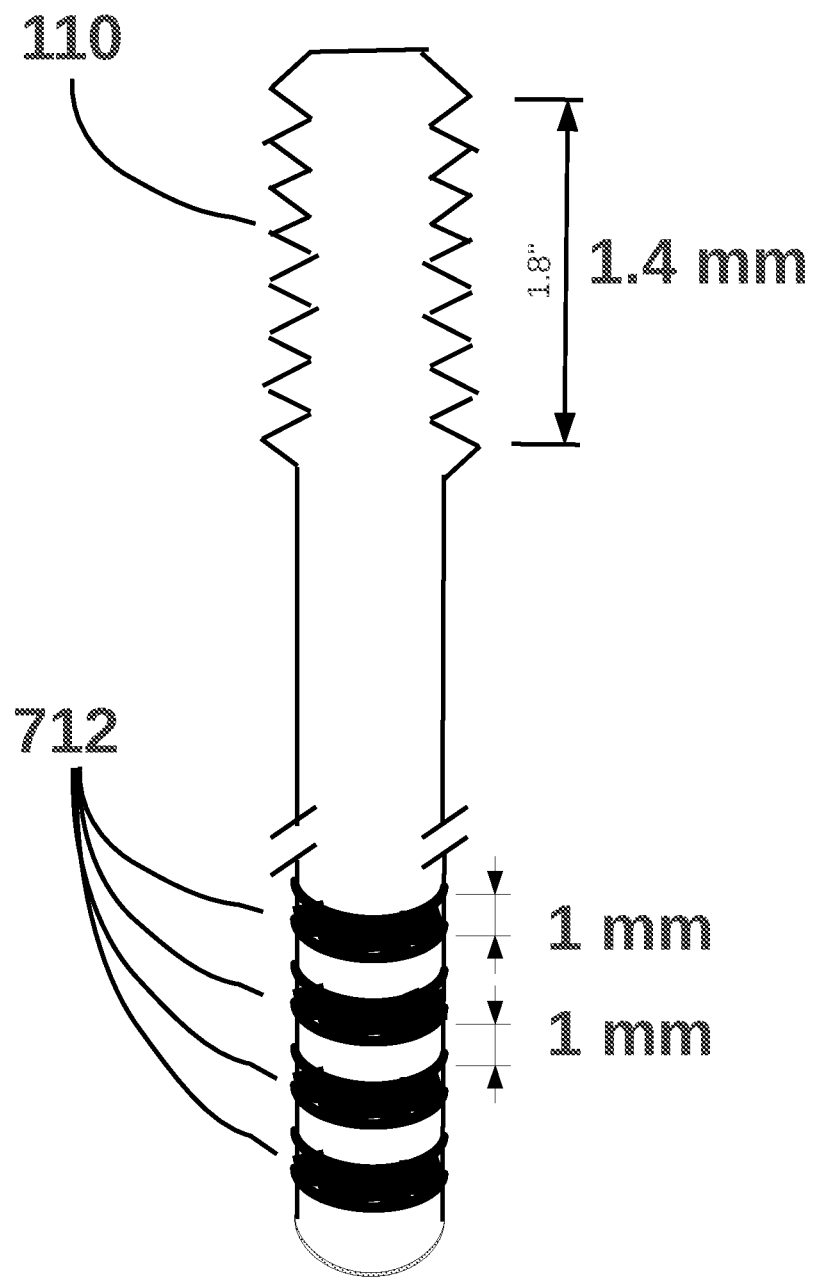

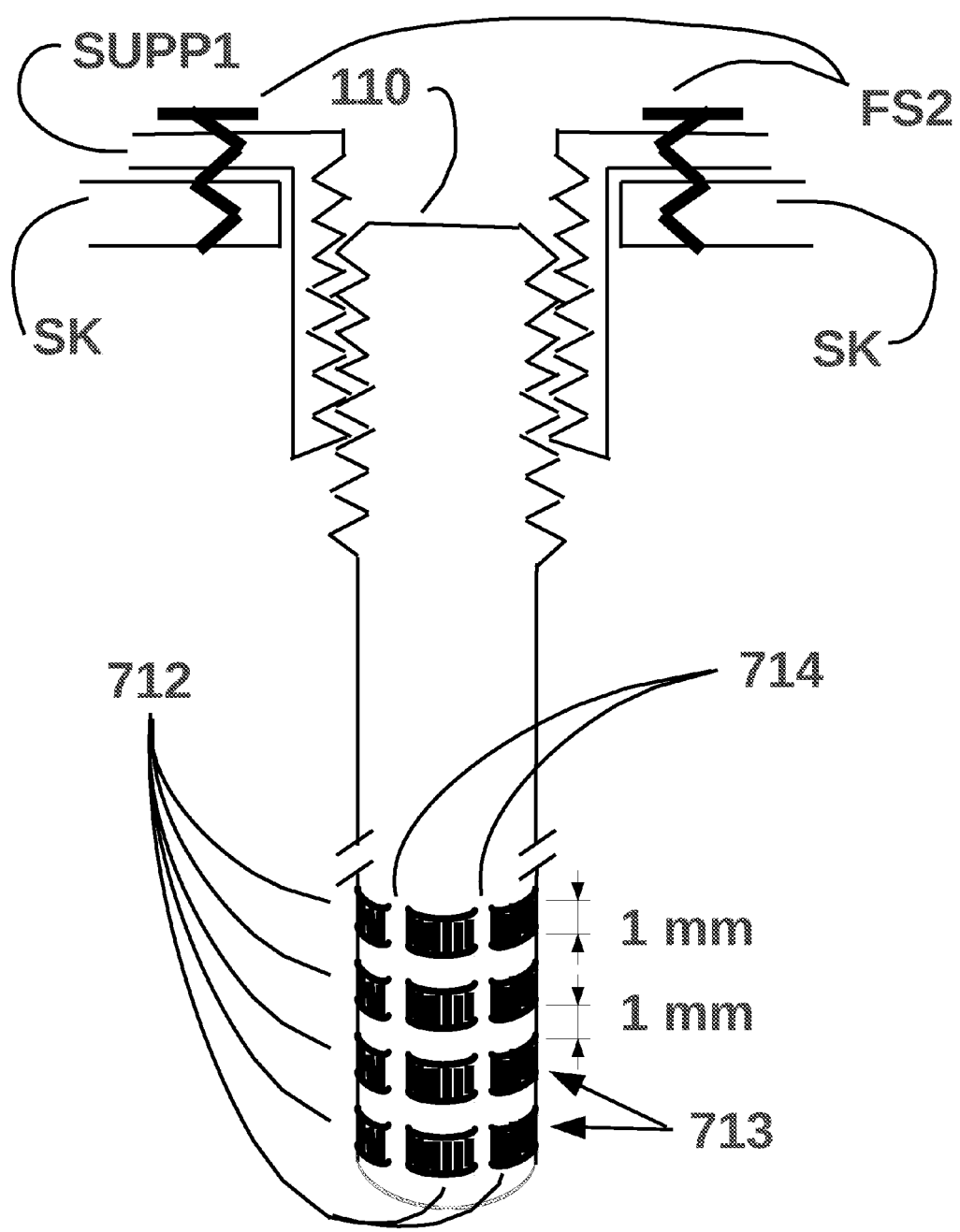

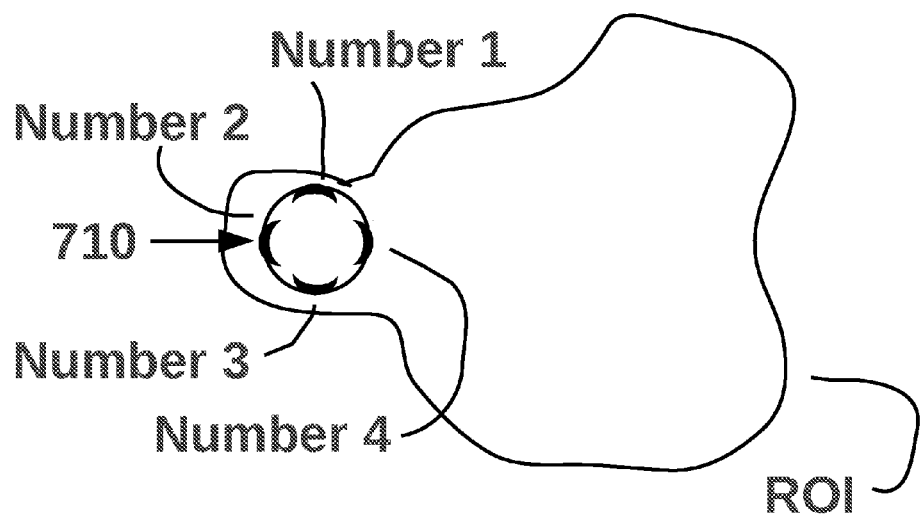
Figure FIG5a
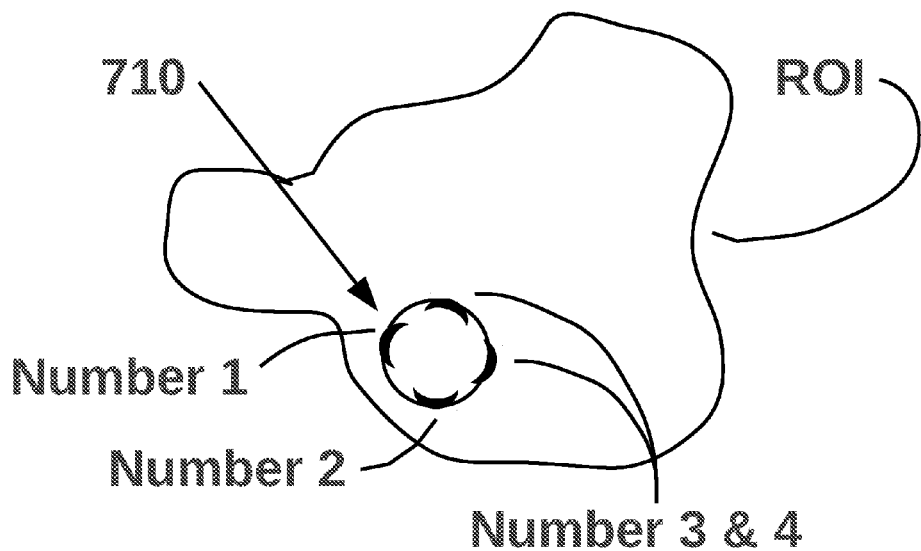
Figure FIG5b

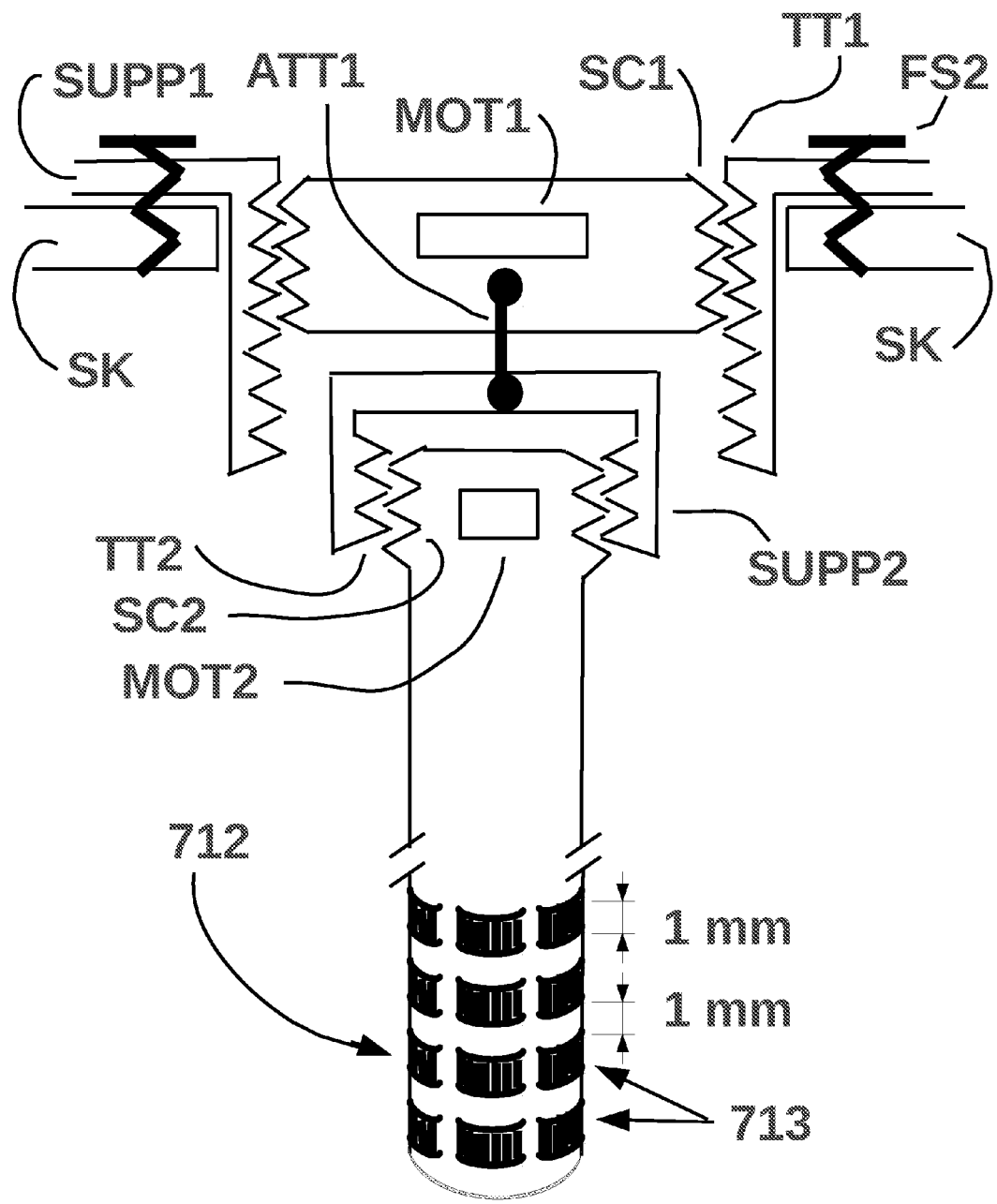

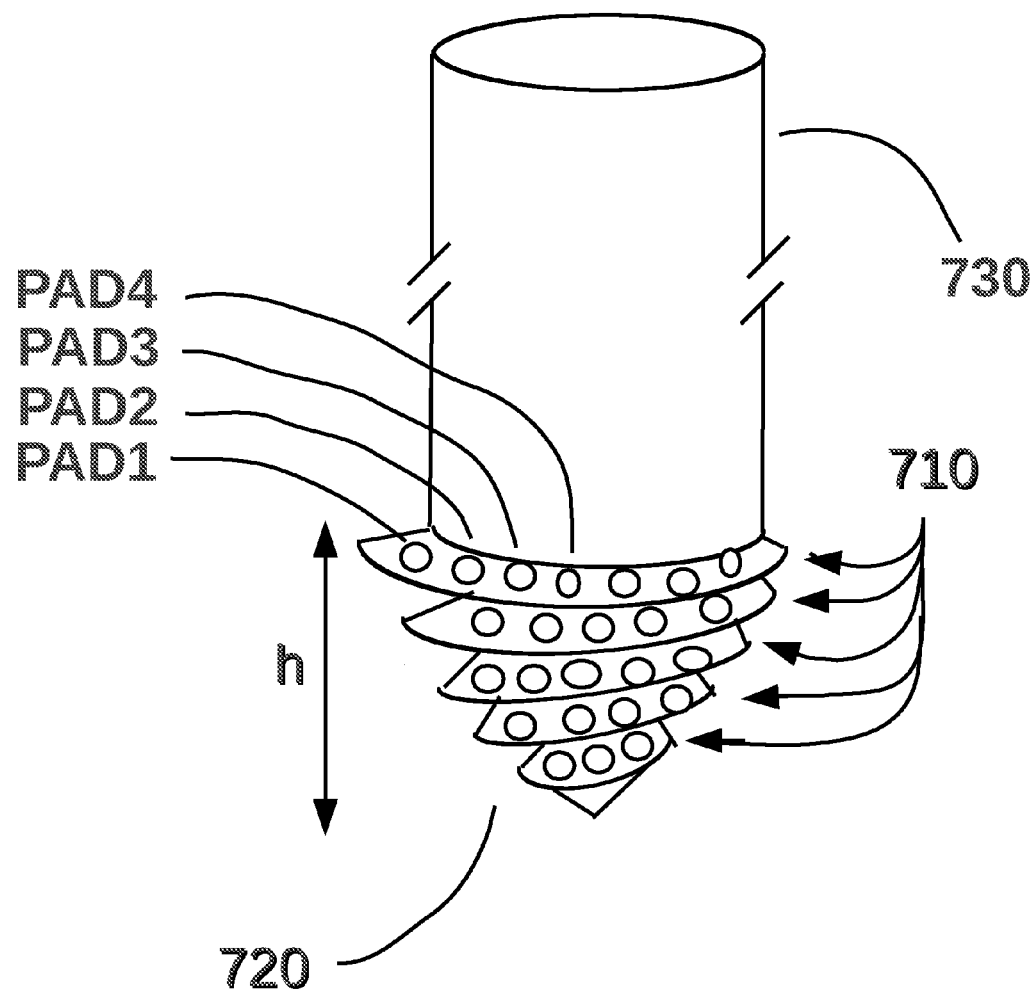

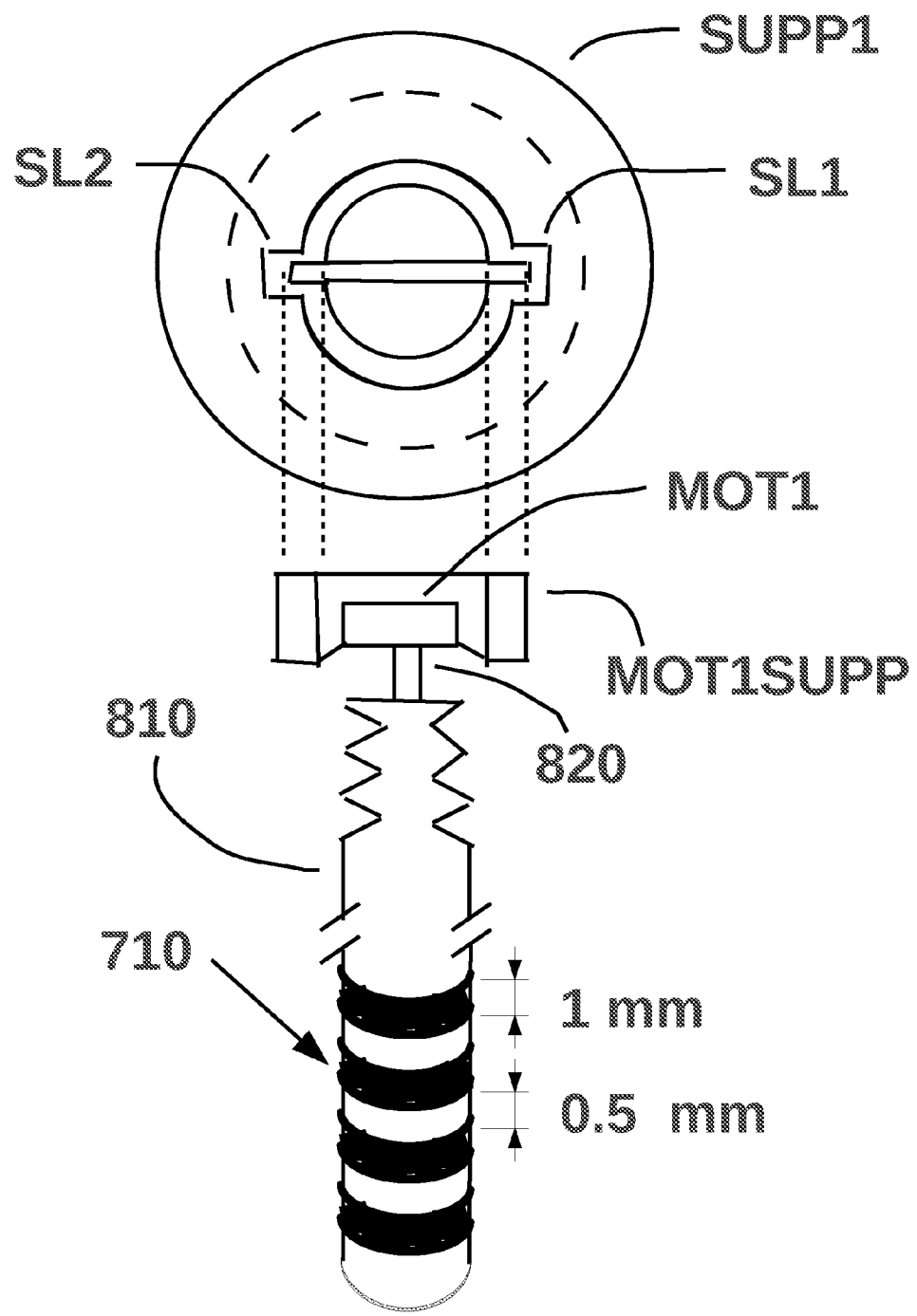

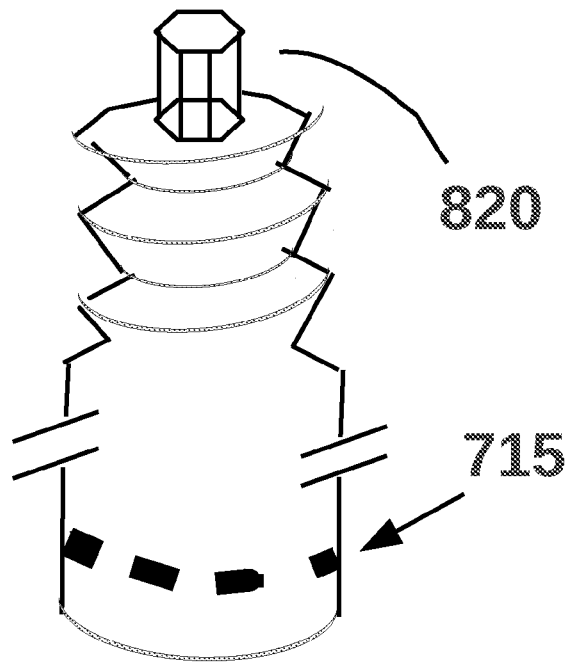
Figure FIG8b
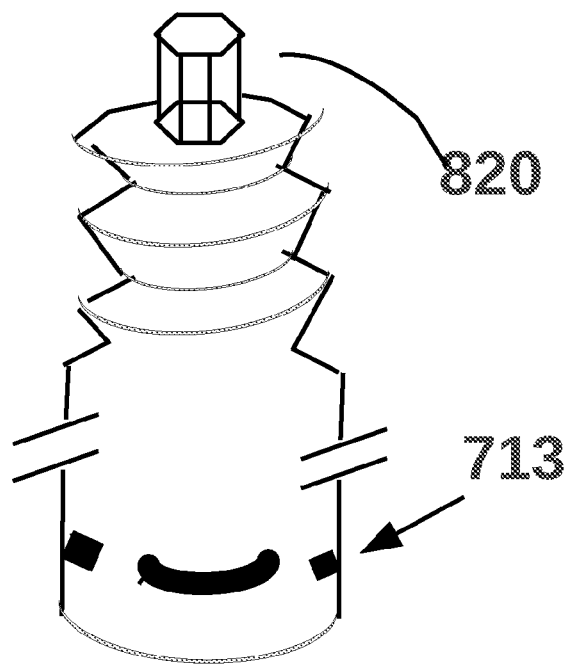
Figure FIG8a

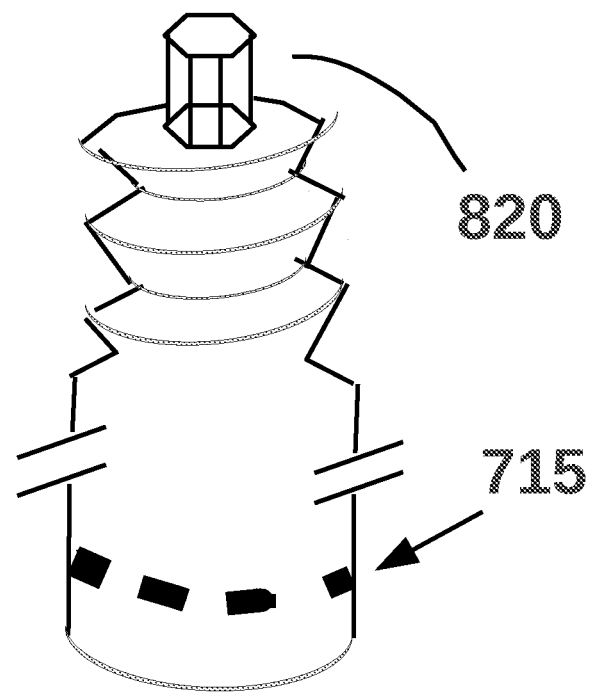
Figure FIG8c

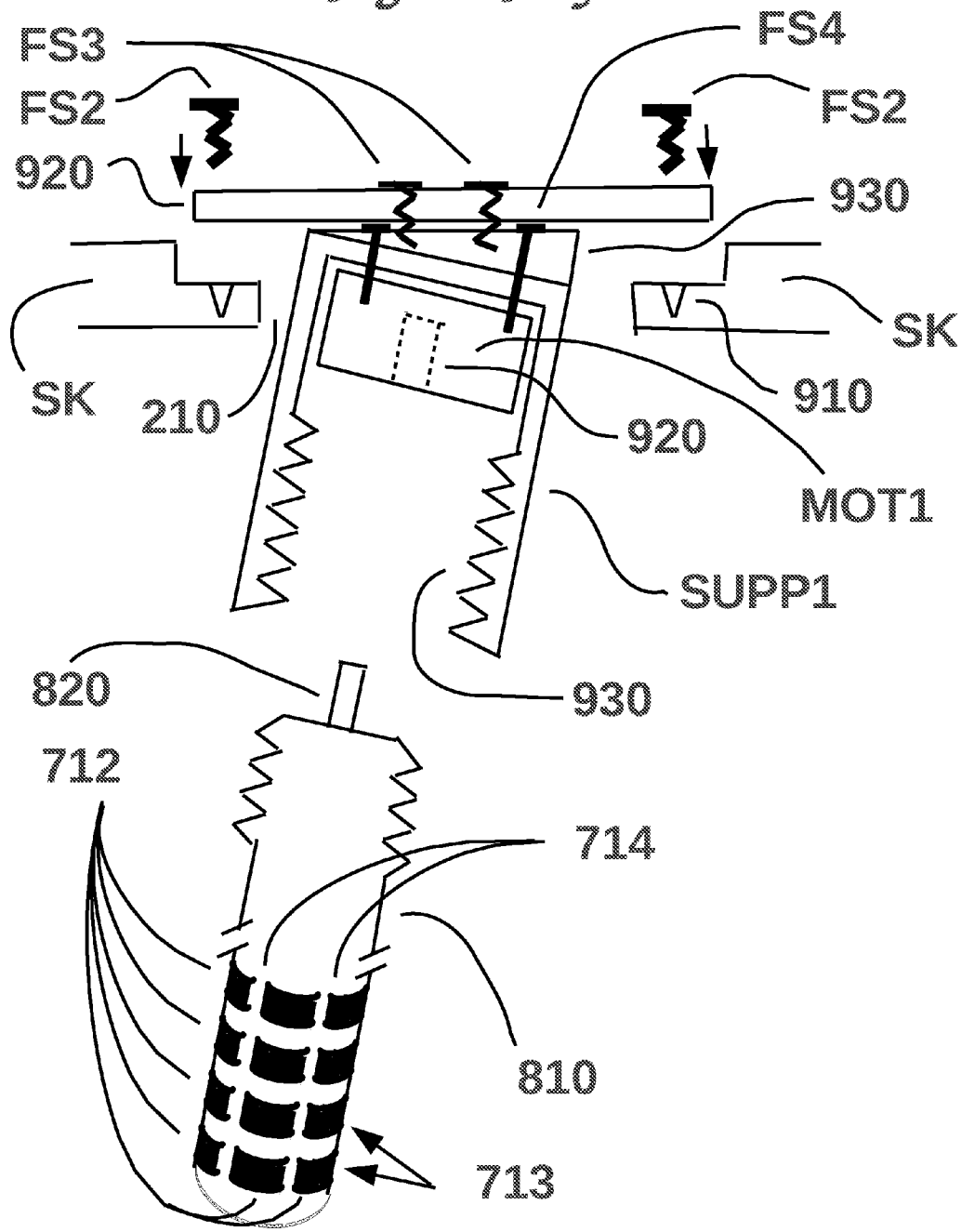

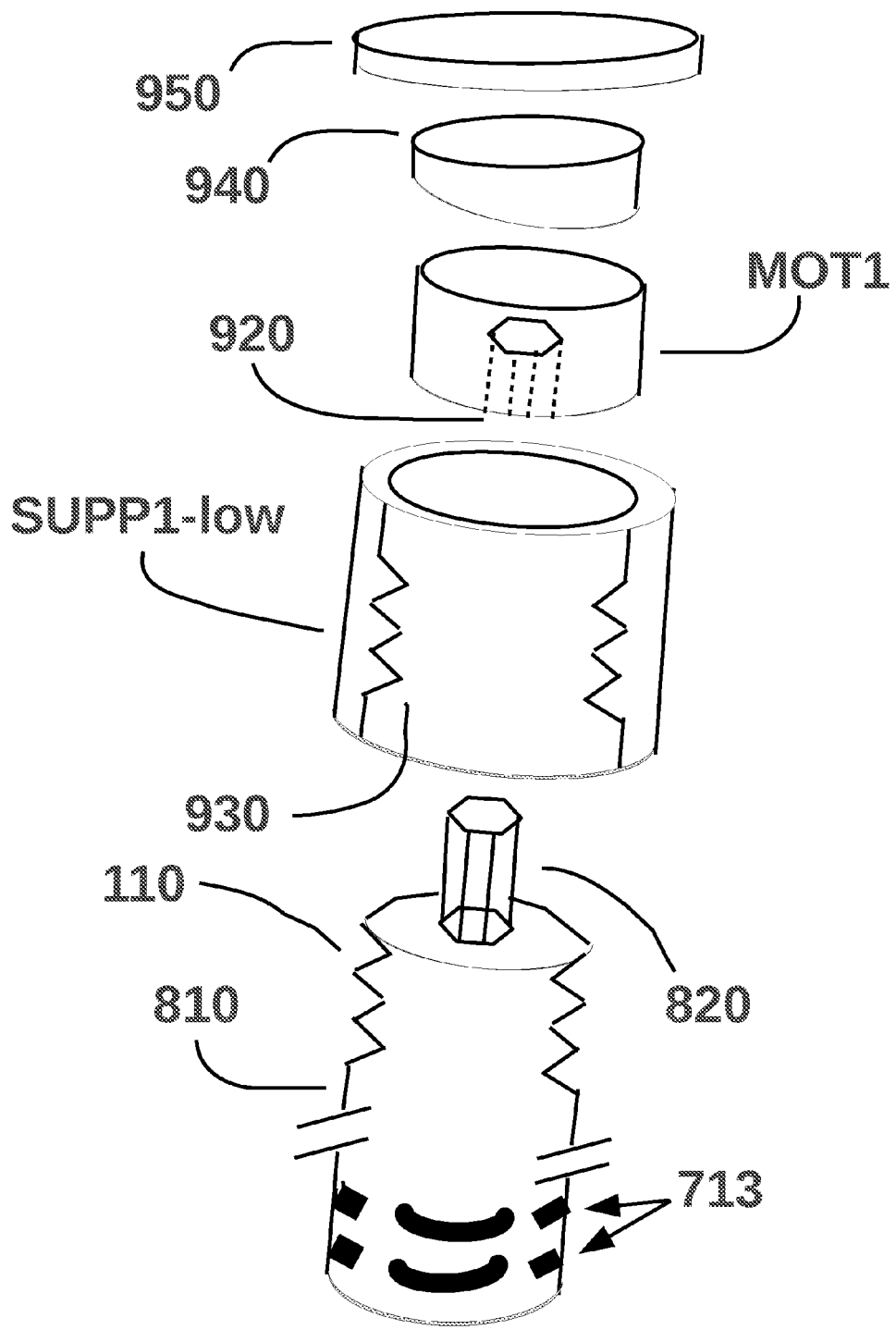

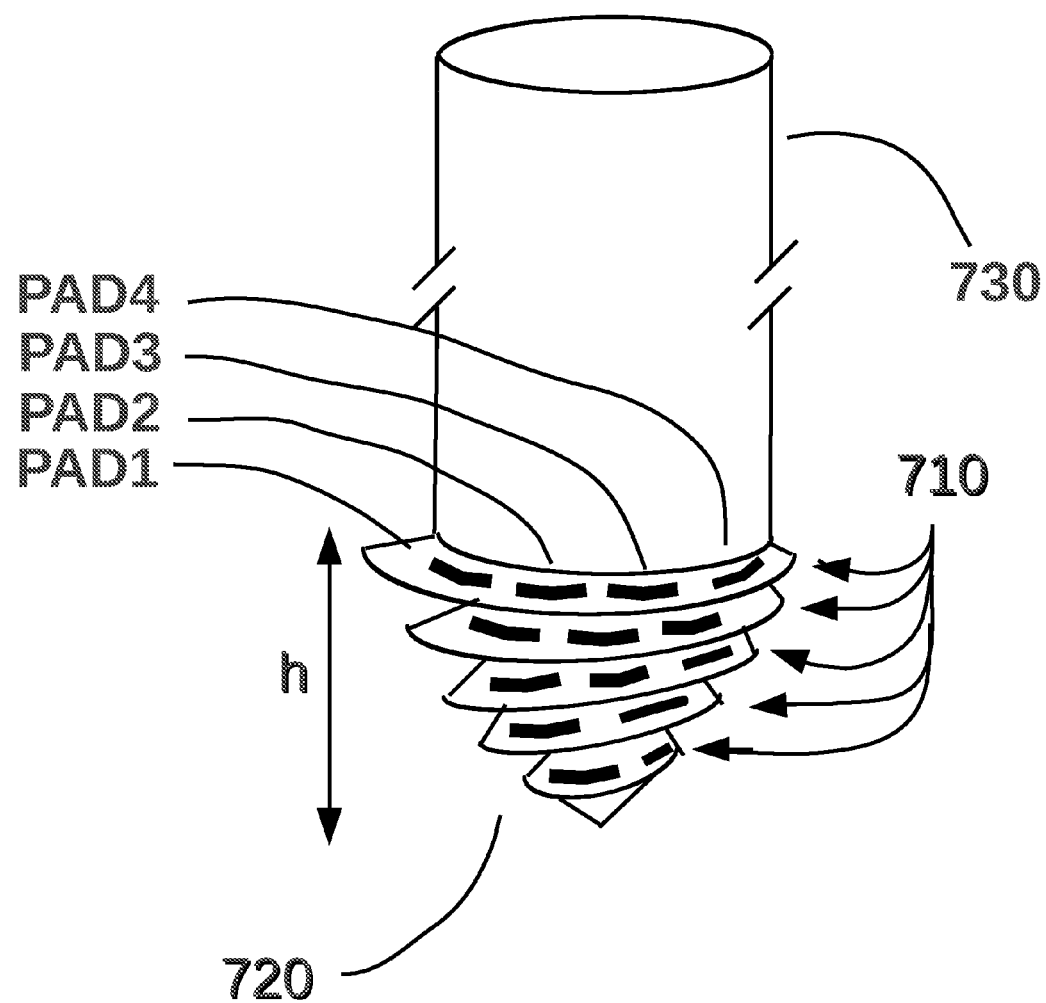

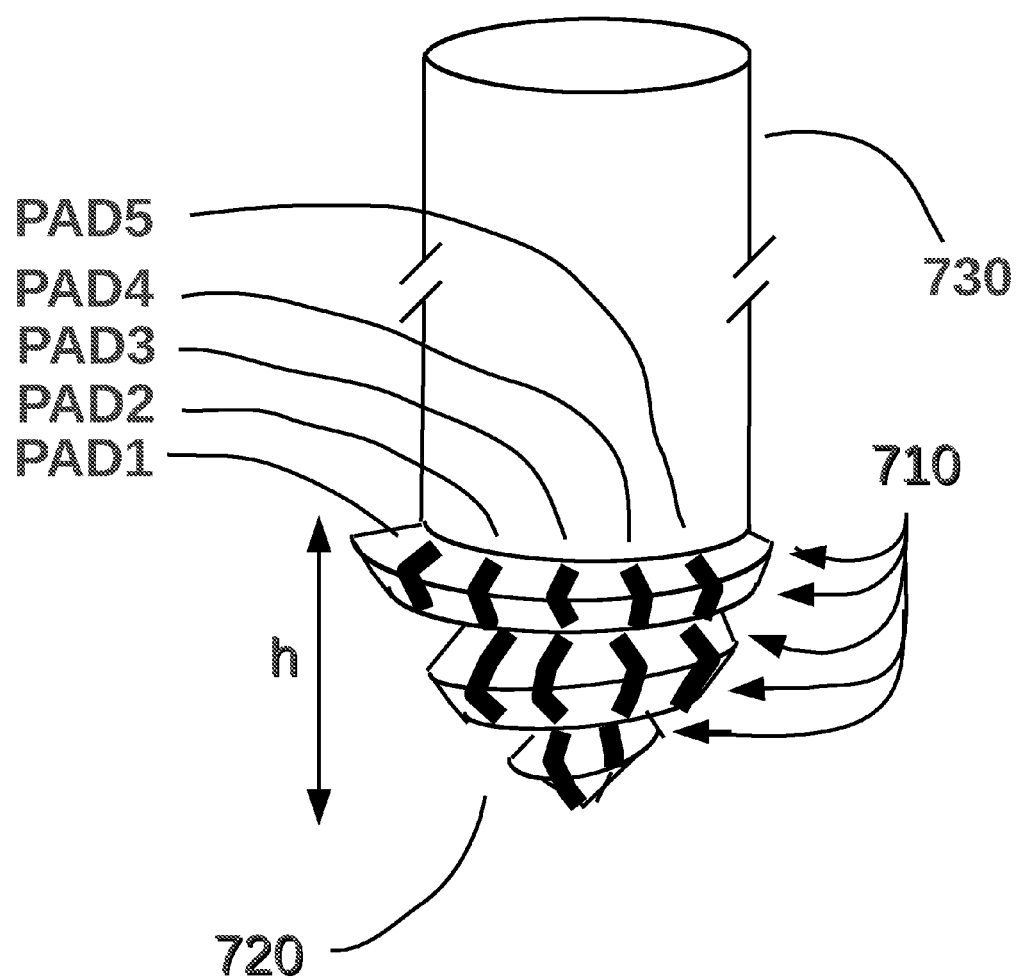

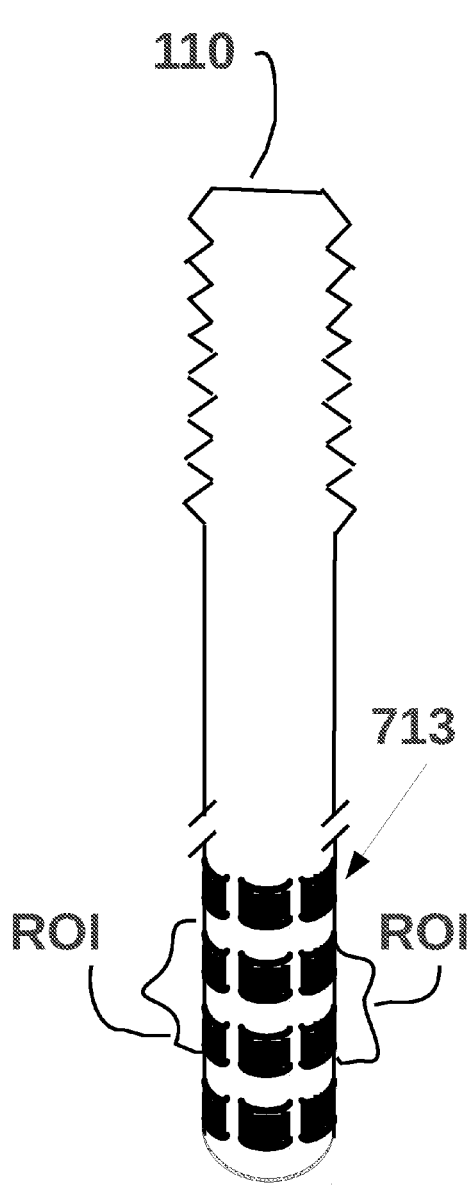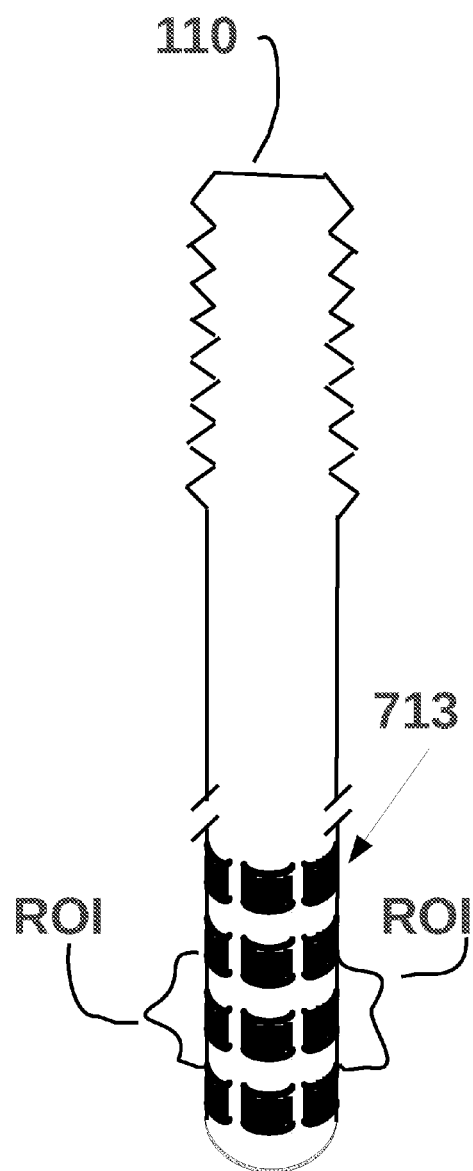

DEVICE AND MEANS FOR ADJUSTING THE POSITION OF DBS BRAIN AND OTHER NEURAL AND MUSCULAR IMPLANTS

CROSS-REFERENCE TO RELATED APPLICATIONS

This application claims priority to U.S. PPA application No. 61/396,334, filing date May 26, 2010 "Method and means to adjust the positioning of stimulating neural and muscular electrode", U.S. application Ser. No. 13/117,132, filed on 2011 May 26, U.S. PPA "Method and means to address and make use of multiple electrodes for measurements and electrical stimulation of neurons and other cells including brain and heart" by Chong Il Lee and Sergio Monteiro, application No. 61/340,920 of Mar. 24, 2010, RPA "Method and means for connecting and controlling a large number of contacts for electrical cell stimulation in living organisms" by Chong Il Lee and Sergio Monteiro, application Ser. No. 12/586,763, of Sep. 28, 2009, RPA "Method and means for connecting a large number of electrodes to a measuring device" by Chong Il Lee and Sergio Monteiro, application Ser. No. 12/586,562, of Sep. 24, 2009, which are included as references in their entirety.

FEDERALLY SPONSORED RESEARCH

Not applicable.

SEQUENCE LISTING OR PROGRAM

Not applicable.

BACKGROUND OF THE INVENTION

1. Field of Invention

This invention relates to cellular electrical stimulation in general, for animals, including humans, and neuronal and muscular electrical stimulation in particular, for brain, spinal cord, peripheral nerves, and muscles, as heart and artificial limbs.

2. Discussion of Prior Art

It is well established that the nerves work as a electrical conductor, neural information being simply electrical train of pulses—short burst of pulses repeated at short time intervals, potentially followed by a longer pause. Measurements on animals have shown that the brain works the same way, and in the few cases in which measurements have been made in humans, it has been confirmed that *H. sapiens* brain is also an electric machinery. The brain acts also as a network creator using synaptic generation and strengthening.

It follows that control of the electrical path of neurons in the brain, and flow of electrical current through its cells can potentially affect the brain activity, whether it be related to motor control, to emotion arousal or just a thought pattern. Among the clinical possibilities, mechanical failures has been the most successful so far, and among these, control of Parkinson's Disease is a case. Parkinson's Disease control is not the only one, some other similar motor control being very successful too, as epilepsy and essential tremor. Other cases are now under evaluation, as depression and eating disorders, to mention just two examples. Electrical stimulation is also used to control pain, as in TENS devices, to control incontinency and potentially any other neuronal malfunction. And naturally that electrical stimulators are also used to adjust the heart beating with the pacemaker, which is one of the oldest application of electrical stimulation.

As an exemplary case we will take the DBS (Deep Brain Stimulation) for Parkinson's Disease control, which is one of the most successful today, with several thousand surgeries performed yearly. The success rate is nevertheless less than what could be. Some of the failures are due to side effects, which may well be a consequence of incorrectly placed stimulators, as acknowledged by many neurosurgeons, including in this case stimulators placed other than the exact center of the target area. The reader should keep in mind that the word "area" in brain means what is normally called a volume; it happens that the neurons that participate together for a particular function are generally connected on a network that is mostly flat (2-D), with little depth ($3^{rd}$ dimension), which is the origin of the word usage. Ultimately this word usage is adopted even when a particular "area" happens to be actually volumetric (that is, having a non-negligible 3' dimension). Indeed, it is very difficult for the neurosurgeon to place the stimulating electrode in the correct place, deep inside the brain and not even open to visual inspection. Current art, for example, the stimulating electrode manufactured by Medtronic (REF_Meditronic_nd) attempts to adjust the final stimulating position offering 4 ring-like stimulating elements, which are at the end of a wand, called "lead" by Medtronic (which we call picafina), each of which can be independently chosen as the stimulating element. The rings are approximately 1 mm in width and separated by 1 mm too. Consequently, after insertion of the picafina in the patient's brain, it is possible to chose the stimulating site with the picafina in the same position, just connecting one ring or another ring to the electrical pulse circuit, while disconnecting the others, or to choose two rings, or many other possible combinations of rings. This final stimulating positioning adjustment is made after the surgery, to compensate for the expected inaccuracies of initial position of the picafina with respect to the desired placement in the brain. Stimulating ring selection can be also needed to compensate for later possible motion of the picafina with respect to the brain. Unfortunately, the picafina must be of small size in order to minimize injure to the brain tissue, which in turn precludes many wirings running through it, this being one of the reasons for the current devices having so few stimulating pads (or rings, or electrodes) which offer so few options for the origin of the stimulating pulses. Indeed, many neurosurgeons would like to have more options, more electrical pads to choose as initiation points for the electrical stimulation, but a solution for this problem was never found. One possible solution is disclosed in patents applied by some of us (INV1, INV2, INV3, INV4, INV5), but alternative solutions exist too. Our invention offers an improvement on this positioning of the stimulating electrodes, and an improvement independent of our earlier inventions cited on this subject.

It is worth to point out that the prior art is capable of initiate an electrical stimulation from any of the four rings, therefore offering a small (1 mm.) adjustment on the stimulation site, but it is not capable of offering adjustment on the stimulation site from the position where one of the ring is to another site where the insulator spacer is. If the ideal position of the stimulator happens to be where one of the separators are, either one of the two adjacent rings have to be selected, of both of them, but no more precise than this. Neither can prior art cause the stimulation to be along one direction only, though the authors are aware of one lead manufactured by Medtronic which sports a small number of isolated pads, which are not circular around the lead but more-or-less rectangular on the surface of the lead.

A similar problem is encountered by heart pacemakers. A pacemaker have to deliver electrical pulses to some particular point in or near the heart. Typically the delivery point is nowadays in the inner wall of the heart, but this is not necessarily so, some pacemakers being attached to the external wall of the heart too. There are malfunctions that are better treated with a dual electrode, and more than two electrodes may become common in the future. Some of these electrodes are inserted via a vein accessed near the neck into the inner wall of the atrium, or upper heart chamber, where the delivering electrode is screwed in the inner wall of the atrium for spatial stability and consistency of electrical delivery point. In current art devices, the tip of the flexible device is made of some electrically conductive material, which is connected by wires to a battery/electronic circuits, which are located elsewhere in the patient, usually the upper chest. Old art has the disadvantage that the electrical pulse is injected over the whole, or at least most of the volume of the attachment. This has the disadvantage that the pulse is injected over too large an area into the heart muscle to be able to control its propagation time, which is needed for a proper, sequential contraction of the heart muscle, needed for optimal pumping. If the electrical pulse is not injected correctly, then the heart pumping is not sequentially squeezing the blood forward, as needed, causing a non-optimal pumping.

Regarding the position, it is not necessary to attach the electrode to the atrium, and our invention should not be limited to this case. In this case the pacemaking pulse is delivered symmetrically around the screw, 360 degrees around it, and it is delivered by all the metallic (or conductive) part of the tip of the device. Yet, such symmetrical delivery is not desirable, because the normal, natural electrical pulse is known to travel through the heart along certain paths with specific speeds and delay times, starting from the sinus, these speeds and delays being a function of the electrical characteristics of the heart muscle, known in electrical engineering as resistance, capacitance, inductance, etc. Normally the pulse initiates from a nerve that delivers it on the coronary sinus, and from there the electrical pulse propagates with speeds that depend on the tissue properties along each direction, which is a much studied problem. This point of delivery is a problem that has not yet been solved, in spite of it being a known source of problems with the pacemaking pulse. Indeed, if the electrical pulse from the pacemaker is delivered in the wrong place then the heart will not beat correctly, because the contraction, which must happen in a particular sequence will not be correct. A good example of the problem is the analogy with a milkman, who must start squeezing the teat near the udder, with his pointing finger (which is usually the one closer to the udder), then the middle finger, then the annular finger, then the small finger by last, if the milk is to be extracted from the utter through the teat. If he reverts the order, or change the other in any way, either no milk at all, or at most less milk will be squeezed from the caw. The pathways for the electrical pulses that originate at the sinus node are well known and it is well known that replication of the natural electrical pulse would be ideal, but an ideal that has eluded the devices in current use. Ideally the heart surgeon would be able to precisely control the depth on the heart wall and direction of delivery of the electrical pulse, as opposed of the voltage only, which is the only controllable value in current art, which also delivers the pulse on all directions, which is not ideal either.

3. Objects and Advantages

One of the advantages of this invention is to adjust the position of the brain stimulation to the best place to cause optimal results for the patient.

Another advantage of this invention is the decrease of side effects due to mis-positioning of the stimulating picafina.

Another advantage of this invention is the adjustment of the depth of penetration of the electrode screwed into the inner wall of the heart (atrium or otherwise), in order to deliver the pacemaking pulse at a precise depth and on a particular direction, adjusted to the particular patient's case, in order to provide a better pulse timing and delay, to ultimately create a better possible contraction sequence of the heart muscle therefore improving the heart pumping capability.

2. Another advantage is the possibility of controlling which said tips are on or off without using a dedicated wire to each said tips, because there is not enough room in the body of the supporting structure for many wires. We propose the use of digital addressing the tips, so a smaller number of wires (say n wires) can select a larger number of electrode tips (2 power n electrodes). Using serial addressing the number of wires can be further decreased to a minimum of 2 wires, or 4 wires if using USB standards, or some similar small number, depending on the standard selected.

SUMMARY

We disclose a method and a means to fine adjust the position of electrical stimulating electrodes with respect to neurons, as in brain or spinal cord, or with respect to muscle, as in heart, with the objective to originating the electrical stimulation at a more precise location with view of improving its effect and of eliminating possible side, unwanted effects. In Brain, spinal cord and the like, our invention is capable of better selecting the neurons that are stimulated, in heart out invention is better able to produce a better heart squeezing sequence, thereby producing a more efficient heart pumping, when compared with prior art.

DRAWINGS

FIG. 1 shows a general view of the main embodiment of our invention using most of the current art features but with a translation feature capable of moving the picafina in and out of the brain. In this embodiment the motor can advance or retreat the picafina by approximately 140% of the distance that separates each stimulating ring-like pad at its distal extremity. The extra motion (40%) being to account for engineering safety, it being possible to have more or less safety margin without changing the substance of the invention. It is possible to advance or retreat by only 100% of the distance between electrodes, but in this case there would be no margin of error, usually not chosen by engineers. It is also possible to advance or retreat by less than 100%, but in this case not all points would be covered; it would be an improvement on the current art but not as complete an improvement as possible to make.

FIG. 2 shows a view of the proximal end of the picafina of our invention. In this particular case there are three holding screws but the same invention would work with more or with less holding screws, as it will be apparent to persons skilled in the art of mechanics.

FIG. 2a shows a top view of a skull with two burr holes for two implants, on the left and on the right brain, one of them showing the support device SUPP1, the other not showing SUPP1.

FIG. 3 shows a general view of the main embodiment which consists of an old art DBS lead, same dimensions as old art, 1 mm wide rings near the distal edge of the lead, separated by 1 mm distance. In this embodiment the screws are also 1 mm long (or 1.4 mm long with the 40% safety margin included), to permit that the metallic electrode rings travel over the 1 mm separating distance between each ring. With this dimensions, the lead covers a total of 5 mm possible positions to initiate the electrical pulses, some of these selecting one or another of the four rings, others by advancing/retreating the picafina device.

FIG. 4 shows a possible configuration of the picafina of our invention with the screw and tapped support and electrodes.

FIG. 5a and FIG. 5b show two possible relative positionings of the picafina with respect to the area of interest. In FIG. 5a the medical staff would turn on electrode number 4 only, to send electrical pulses towards the area of interest, while in FIG. 5b electrodes 3 and 4 would be energized, for the same reason. Note that FIG. 5 (a and b) display the relative position of the picafina of our invention with respect to tissues perpendicular to the main dimension (or theta-direction, angular displacement in normal cylindrical coordinates). FIG. 12 (a and b) display the relative position of the picafina of our invention with respect to tissues along the main dimension (or z-direction, displacement in normal cylindrical coordinates). The picafina of our invention allows for better adjustment of the stimulating point in both angular (theta) and axial (z) coordinates.

FIG. 6 displays an alternative embodiment of our invention in which there are two independent motors MOT1 and MOT2, each of which are capable of providing a rotational motion. Due to its particular mechanical connections, as common and known in the mechanical arts, MOT1 causes attachment SUPP1 to move axially, perpendicular to the skull, which then, through attachment ATT1 moves the second support SUPP2 up and down, together with SUPP1. ATT1 is capable of imparting translational motion to SUPP2 but not to rotate SUPP2. Rotational motion is independently imparted to the picafina of out invention by another motor MOT2, which turns the picafina supported by SUPP2. In this particular embodiment the electrical pads are shown as making an arc of 80 degrees each, with 10 degrees separation between each electrical pads, making a total of four pads around the circumference. The total number of pads in this embodiment is 16 (4 pads along each ring and 4 rings separated by 1 mm from each other). The number of electrical pads can be larger or smaller without changing the disclosure of the invention. For example, another embodiment could have 8 pads on each ring, each one encompassing an angle of 35 degrees, separated by 10 degrees, and more or less than four rings are possible without changing the principle of the disclosed invention.

FIG. 7. Distal extremity of the heart stimulator, or pacemaker device, here called cordum, with the multiple pads, or electrodes, which are the location from which the electrical pulse originate. The pads are selected with a digital or binary addressing system, as described in other patent application of some of the authors of this patent, which can be sent either in parallel or in serial form. The length indicated, h, shown as being between 1 mm and 10 mm, but these are just typical values, not intended as a limitation on the invention, as can be appreciated by the practitioners of the art, longer and shorter values are possible, depending on the particular situation, heart wall thickness, etc. The angle of the screw is also not a limiting parameter, the drawing simply indicating a possible embodiment out of a large number of other values, as it can be appreciated by the practitioners of the art.

FIG. 8, FIG. 8a, FIG. 8b display details of possible anchoring mechanisms for the motor and proximal extremity of the picafina of our invention. A connecting axle CON-AXLE with a hexagonal shape at the picafina, matches an hexagonal orifice at the distal extremity of the motor MOT1, similar to the standard hex screw drives and screws. Note that it is not necessary to have these parts with hexagonal shape, as a slot (similar to old screws and screw drives), or a cross (similar to Philips screws and screw drives), and star (similar to star screws and screw drives), etc. are equally acceptable, as it is appreciated by persons with knowledge in the art of mechanical connections.

FIG. 8c displays a longer CON-AXLE at the proximal extremity of the picafina of our invention, which can take the vertical motion in-and-out of the brain without decoupling from the motor. It is possible to use such a method which then keeps the motor MOT1 fixed, as opposed to FIG. 8, in which the motor MOT1 moves up and down along the slots SL1.

FIG. 9 displays a mechanism to allow for the insertion of the picafina at a position other than perpendicular to the skull. Often times the picafina is inserted at a small angle with respect to the perpendicular to the top of the skull (call this perpendicular "vertical"). A mechanism indicated allow such an adjustment to be made, as needed by the surgeon. Note the angle adjusting wedge ANG1.

FIG. 10 shows a blow-out of several of the parts shown in FIG. 9

FIG. 11 (a and b) show alternative possibilities for the cordum, used for heart pacemaking.

FIG. 12 (a and b) show the effect of the vertical (or z-direction, along the main dimension of the picafina) mis-positioning of the picafina with respect to the region of interest, and the effect of our invention in correcting it. The reader is encouraged to refer also to FIG. 5a and FIG. 5b, which display the mis-positioning in the theta direction. Saying it in another way, FIG. 5 displays mis-positioning due to the picafina being on the side, or edge of the region of interest, while FIG. 12 displays mis-positioning due to the distal extremity of the picafina being beyond the region of interest. The former case (theta) requires that only part of a ring be selected, the latter case (z) requires that the ring in use be as close as possible to the center of the region of interest along the z-direction, or the long dimension of the picafina. Note too that for the z positioning, it is the best positioning that is sought, which is achieved with our invention disclosed here. Here we are using z and theta in the ordinary sense used by mathematicians to describe cylindrical coordinates.

DRAWINGS—LIST OF REFERENCE NUMERALS

EM1=electric motor which causes the translational motion of the picafina along its length FS2=Fixing screw, which fixes the supporting structure SUPP1 onto the skull.

Skull=self describing.

EM1=motor capable of moving the picafina.

EM2=motor capable of rotating the picafina of our invention.

MOT1=motor capable of moving the picafina.

MOT2=motor capable of rotating the picafina of our invention.

SUPP1=supporting structure, screwed onto the skull, which is fitted with a means to slide the picafina in and out of the supporting structure. In the main embodiment such a sliding motion is made by a screw.

SUPP2=supporting structure, attached to SUPP1, which serves as a support for a rotating device caused by MOT2

SR1=screw on the proximal end of the picafina of our invention.

TT1=tapped thread on SUPP1 inside which SR1 turns to move the picafina of our invention along its longitudinal dimension.

DETAILED DESCRIPTION

Preferred Embodiment—FIG. 1, FIG. 2 FIG. 2a, FIG. 3, FIG. 4, FIG. 6, FIGS. 8, 8a, 8b, 8c, FIG. 9, FIG. 10 and FIGS. 12a,b We will describe a main embodiment of our invention for use in DBS (Deep Brain Stimulation). Variations for use in more superficial areas of the brain, or for use in spinal cord, or for use as TENS devices (Transcutaneous Electrical Nerve Stimulation, pain control), or for use as heart pacemakers, etc. will be apparent to the ones skilled in the relevant arts.

We firstly make a shorter description intended for engineers and technicians, then a longer description for the layperson, or a person who is familiar with some of the aspects of the invention but not familiar with all of its aspects. Note that the invention involves more than one fields of expertise, so the number of people familiar with all its aspects is small.

Explanation for engineers and technicians. The theory discussed here is believed to be true, but the invention is not dependent on its truth, but only on the effects, which are amply verified by practice. The theory is discussed only to cause the reader to better understand the subject matter and the working of our invention. Deep Brain Stimulation is the name given to the insertion of carefully controlled electrical pulses in a precise position in the lower, or deeper part of the brain. The location is not an arbitrary choice, but it is rather the location that controls, or at least is involved in some way, with the particular characteristic that the neurologist want to modify. Given a characteristic to be changed, the position (or positions) in the brain which should receive electrical stimulation is fixed. This is because each thing originates in a particular place in the brain, whether it be mechanical, like the motion of an arm of the jaw, or emotional, as a feeling of love or fear, each one originates in one of several defined and known parts in the brain. Parkingson's disease depends on neural firings in a few positions deep inside, at the base of the brain, from where the name of the surgery originates. It turns out that it is difficult for the neurosurgeon to position the electrode at the exact target position, both because the desired place is very small, and also because the relative position of it, with respect to a fiduciary, fixed position on the skull is variable from person to person, similar to the position of the tip of the nose being different, with respect to each ear lobe, from person to person. Ultimately the neurosurgeon knows that the placement of the picafina is only approximate. Old art solved this problem offering a choice of 4 rings (or some similar arrangement) to chose after the surgery finishes, each ring offering a different location for the electrical stimulation. The improvement of our invention over prior art is partly the ability to move the picafina in-and-out, along its length, in order to produce the stimulation at the perfect position (FIG. 1). Another improvement of our invention over prior art is the possibility of producing the stimulation not along all directions (360 degrees around the picafina distal end), as most of prior art devices do, but along selected directions (see FIG. 4), as needed and discovered by experience, each patient requiring a particular stimulation. Our device offers the possibility of rotating the picafina along its main dimension to position the stimulating pads towards the optimal directions, as discovered by experience with each patient. The most simple embodiment of our invention uses one motion device only, while a more sophisticated version uses a minimum of two motion devices, one to move the picafina in-and-out of the brain, the other to rotate the picafina, in order to cause the stimulation along the most desired direction (see FIG. 6). The combination causes the stimulation to be delivered at any desired depth and along any desired direction, as needed for any particular patient making use of the device.

We will now describe a main embodiment of our invention for laypersons, also for use in DBS (Deep Brain Stimulation). Variations for use in more superficial areas of the brain, or for use in spinal cord, or for use as TENS devices, or for use as heart pacemakers, etc. will be apparent to the ones skilled in the relevant arts. FIG. 1, FIG. 2 FIG. 2a, FIG. 3, FIG. 4, FIG. 6, FIGS. 8, 8a, 8b, 8c, FIG. 9, FIG. 10 and FIGS. 12a,b display simplified views of the main embodiment of our invention for DBS. In FIG. 1 one can see a supporting structure SUPP1, which is fastened onto the skull by fixing screws FS1 (there are three screws in this particular main embodiment, but the equivalent results can be achieved with more or less fastening screws, as known by the people familiar with the art). On supporting structure SUPP1 there exists a tapped screw, or auger, which is part of the means to move a picafina-like device along its long dimension, in and out of the patient brain. This particular method is shown as an exemplary implementation only, as there are many methods which can achieve the same result of moving a piece axially, as known to the people familiar with the art of mechanical motion, as machinists with experience in lathes and milling machines, automobile repairmen, mechanical engineers, "handymen", or even to lay persons. One of the improvements of our invention over prior art is the capability of moving the picafina used in DBS into and out of the brain, as well as turning it around once inserted, to change the position and the direction of its electrodes or pads, from where the stimulating pulse originates. This particular implementation of a translating device using electric motor EM1 and EM2 is not the only possibility for our invention, which is not the invention of an electric motor, not the invention of a translation device, nor the use of a rotation device, but rather the use of a rotation device and of a translation device to achieve the goal of moving a picafina-like device to adjust the precise position of the delivery of the DBS pulse to the desired brain location. This adjustment is required by two factors. First the neurosurgeon cannot insert the picafina into the optimal position, which results that adjustments have to be made post-surgery to the stimulation site, and second because the picafina may move with respect to the brain, or vice-versa, needing later adjustment to correct for this. In one possible main embodiment there exists on the proximal end of the picafina a thread matching the female thread on supporting structure SUPP1 and an electrical motor to turn this thread. In other words, this means to move the picafina along its long dimension is an auger with female part on SUPP1 and male part on the picafina itself, with an electric motor on the picafina which is capable of turning the male part of the auger (the part connected to the picafina), which then moves the picafina along its long dimension. In a second possible main embodiment, shown in FIG. 6, there are two electrical motors, EM1 and EM2, where EM1 causes, due to the coupling, a translation only motion on the picafina, in-and-out of the patient's brain, while EM2 causes a rotation only motion of the picafina, rotating it around its main, long dimension.

In the main embodiment said means to move said picafina-like device is capable to move the picafina-like device over a 1.4 mm range, 1 mm being the separation between the electrode rings, 0.4 mm for engineering safety. This range corresponds to the space separating each of the rings that originate the stimulation electrical current in existing Medtronic electrodes (see FIG. 3) with an added arbitrary engineering safety margin of 40%. The reader will notice that if the screw can longitudinally displace the picafina by the same distance as the ring separation, all the dead space between two rings become reachable by the adjoining rings. Within the confines of the main embodiment, as described, with 1 mm wide rings, spaced by also 1 mm, at the distal end of the picafina (see FIG. 3) a 1 mm range of motion causes a total reach of 5 mm (discounting the added 0.4 mm safety margin) with the resolution (minimum longitudinal dislocation) of a few micrometers, equivalent of the advance corresponding to the minimum angular turn of the supporting structure and the screw pitch, which is not specified in this description but can easily cause a minimum longitudinal motion of 50 micrometers, roughly equivalent to a hair width. The invention preferred embodiment would provide a motion of 1.4 mm, corresponding to a 40% engineering safety margin, though this safety margin should not be considered a limitation of our invention, which works without it. In fact, the invention even offers some improvement over current art even if the motion is not enough to cover the full separation between two of the rings, such a case being also covered by our invention.

FIG. 2 displays a view from the top of the skull, where one can see the burr hole to access the brain and the circular flap SUPP1 which is screwed onto the skull by a plurality of screws. In the main embodiment there are three screws attaching the support SUPP1 onto the skull but persons skilled in the art understand that it is not necessary to use exactly three screws, it being possible to achieve the same result with less and with more screws, three screws being used as an exemplary concrete case which is not intended to restrict our invention.

Finally, FIG. 3 shows the simpler form of the improved picafina of our invention alone, independent of its attaching and moving mechanism. The simpler form is only capable of an in-and-out motion, with an associated rotation as the picafina moves in-and-out. A proximal end with screws used to turn and move it forward and backward, depending on the direction of turn by motor EM1, its elongated body and the four ring-like electrodes at its distal end, from where electricity can be injected in the brain to achieve the desired result. kextra.Some examples of intended use (from another site, another template, good section to add further info and details)

One example of intended use of our invention is for the treatment of Parkinson's disease. For Parkinson's disease the electrical stimulation occurs on either the globus pallidus internus (GPi) or the subthalamic nucleus (STN). For the similar problem known as essential tremor the usual target is the thalamus (T). In either case, the picafina is inserted in the brain until its distal extremity reaches the desired location (GPi, STN or T or other location determined by the neurosurgeon). Once the distal extremity of the picafina is at the desired depth, one or more than one ring is selected, by trial and error, to produce the stimulation, until the desired positive effects are observed. Our invention allows the extra possibility of selecting depths not covered by prior art devices, the depths that correspond to the dead spaces around the spacers between any two ring-like electrode in current art devices. as well as to produce the stimulation along some directions only, as shown in FIG. 5a and FIG. 5b.

Another example of intended use of our invention is the heart pacemaker. One of the possibilities to attach a pacemaker to the heart is to start from a generally neck located vein, from which a wire is inserted down onto the inner wall of the heart, and ultimately the tip of this wire is screwed into this inner heart wall. Prior art pacemakers use the tip of the device to start an electric pulse over a large surface area and symmetrically over the 360 degrees around it. Our invention as shown in FIG. 7, uses a plurality of pads to initiate the pacemaking pulse. Choosing one or a group of electrodes (see FIG. 7) creates a pacemaking pulse at a precise depth on this anchored electrode, and towards any chosen direction, and along any arc angle desired, this being obtained with the appropriate selection of a subset of the electrodes on the cordum of our invention. It is well established in the art that the electrical pulse travels through the heart, usually from the sinus, at a particular speed and phase (that is, delay) along the heart muscle, causing it to contract in a particular sequence, which maximizes its pumping capability. For this pumping to be best replicated, the electrical pulse must be initiated in particular places and directions, which is not done in prior art. Our invention improves on this, allowing the initiation place of the stimulation pulse to be anywhere on the surface of the anchoring part of the pacemaker, at any depth and towards any desired direction. The selection of electrodes is made using a method disclosed in our inventions (INV1, INV2, INV3, INV4, INV5), which are part of this disclosure and are included here in their totality. Some of the pertinent parts of these inventions which are currently in the PPA and RPA stage are included at the end of this PPA for completeness but we request that their full text be considered as part of this disclosure. By the time that an RPA is applied based on this PPA the older PPA will be an RPA, which we request to be part of this disclosure too.

For heart pacemaking the heart surgeon keeps inserting the electrode into the heart wall while observing the results of electrical pulses on an EKG (electro-cardiogram) machine, all the while looking for the best location. Our invention, which has isolated and relatively small electric pads to initiate the stimulating electrical pulses, offers the possibility, not offered in prior art devices, of stimulating the heart at a more defined location, which, in turn, causes a better contraction sequence of the heart.

Operation of Invention

Our invention operates adjusting the position of the implanted electrode both axially (in and out of the brain) and radially (rotation around its long dimension). A combination of these two motions adjust the position of the electrodes for optimal position of the electrical stimulation.

The main embodiment of our invention operates moving axially the picafina of our invention, in and out of the brain, that is, along its major axis, by means of an electric motor EM1, which is located on the proximal end of the picafina, and rotating it around its major axis, by means of another independent motor EM2, to position the pads towards any desired direction. Motor EM1 is capable of turning the screw SC1 inside tapped thread TT1, causing the picafina to advance into or to recede from the brain, depending on the direction the screw is turned—advancing for a clockwise turn of the screw and receding for a counterclockwise turn of the screw (assuming a normal, right-hand screw as intended in the main embodiment, this being only an arbitrary choice, any type of screw being possible to use, including a left-hand screw). Motor EM2 is capable of rotating the distal extremity of the picafina as needed, rotation which is achieved with the turning of SC2 inside TT2, where TT2 is a tapped thread on support SUPP2. This motion of the picafina caused by the rotation of SC2 inside TT2 also causes an in-and-out motion, but the intended purpose in this case is to simply turn the picafina, so the thread may, for example, be fine, and in any case, once the motion is decoupled, MOT2 being responsible for the rotation part of the picafina adjustment, it needs to cause only 360 degrees rotation, or, adding an engineering safety margin of say, 40%, 504 degrees rotation. Persons familiar with the engineering art will immediately understand that a safety margin of 10%, or 25%, or any similar one are also in the scope of the invention, this suggested value of 40% safety margin being used only as an exemplary value not intended to limit our invention.

In the main embodiment motors EM1 and EM2 are located at the proximal end of the picafina, but this should not be taken as the only possibility, as it is readily appreciated by the practitioners of the mechanical arts, it being possible to have, for example, EM1 at the proximal end of the picafina, at the skull, and EM2 at the distal end, just before the electrodes, or any other combination.

Description and Operation of Alternative Embodiments

In an alternative embodiment of our invention the four rings displayed on FIG. 1 are replaced by 16 smaller ¼ rings (approximately 80 degrees arc each), as shown in FIG. 4. Comparing FIG. 1 and FIG. 4 it is seen that each of the four rings in FIG. 1 is split in 4 arcs separated by a small gap between each ring, which may encompass an angle of, for example 80 degrees (exemplary value only, not intended to limit the invention) for the pad and 10 degrees for the gap between any two pads part of the same idealized ring. This allows for the active region to be towards one side only of the picafina device, covering an arc of slightly less than 90 degrees (if only one quarter is used, or 180 degrees (if two quarters are used), or 270 degrees (if three quarters are used), or the full circumference (if all four quarters are used), as needed for a particular case on a particular patient, depending on the particular positioning of the picafina with respect to the area of interest. For example, if after a difficult surgery it turned out that the picafina have actually been placed on the edge of the region of interest, as shown in FIG. 5a and FIG. 5b, then only one or two quarter electrodes would be activated (the single electrode 4 in the case shown in FIG. 5a, two electrodes 3 and 4 in the case shown in FIG. 5b). Persons skilled in the art will note that it is possible to have more than 4 electrodes around the perimeter at a fixed distance from the endings, 4 being used as an exemplary case. For example, a large number of electrodes can be used with a much smaller number of wirings if digital addressing is used, as disclosed in other patents, and the digital addresses can be sent serially, reducing the number of address wires to just 2 (data and return), or 4 if a USB-type of serial address is used, or other small number of wires, depending on the serial protocol used for transfer. These variations for the selection of the pads are disclosed in the invention of some of the current inventors, INV1, INV2, INV3, INV4 and INV5, parts of which are copied below for completeness, but which are included in this invention in its totality.

In an alternative embodiment, shown in FIG. 6, our invention offers the possibility of moving the pads, or electrical stimulation points on the picafina, both translationally along its main axis (in and out of the brain) and rotationally (turning the picafina around its long axis) separately. In this alternative embodiment there are two augers (or screws), one for each motion: translation and rotation. These are shown as the screws (or augers) in supporting structures SUPP1 and SUPP2. In FIG. 6 the screw SC1 of SUPP1 is capable of a displacement of 1.4 mm, to match the separation between the electrodes added by a 40% engineering safety margin, but this motion is coupled to the picafina by attachment ATT1, which is only capable of pushing and pulling the picafina in and out of the brain, but not to rotate it. Therefore the rotation of the screw connected to SUPP1 is not transferred to the picafina. The screw SC2 (or auger) on supporting structure SUPP2, on the other hand, does turn the picafina. In this configuration the screw SC2 on SUPP2 may have a smaller displacement, 360 degrees, for example, which is enough to rotate the picafina to any desired angular position. Again, it is envisaged that EM2 would offer some engineering safety margin of 40%, in which case EM2 would rotate a total of 504 degrees but the invention also works without any safety margin, as well as with a rotation smaller than 360 degrees, particularly if there are several smaller arcs completing the ring-like electrode. For example, the device shown in FIG. 6 has four partial rings encompassing an arc of 80 degrees each, with a gap encompassing a 10 degrees angle. In such a situation the rotating screw SC2 only needs to turn 90 degrees to cover all the possible directions. Persons familiar with the art will notice that the smaller is the arc encompassed by the electrodes, the smaller is the turning required to the turning screw SC2. Such trivial variations are part of our invention.

In another alternative embodiment, herein called planarium, which is intended in applications where the area to be electrically stimulated is generally planar, the device of our invention is correspondingly of a generally planar shape, with an inner and an outer surface, being fitted with electrodes capable of delivering electric currents on one or both of its surfaces. The electrodes in this alternative embodiment may be circular in shape, or may be square or rectangular in shape, and they may be individually connected to an electrical energy source capable of delivering a voltage and current, or they may be selectable by binary addresses, which may be chosen either in parallel or in serial form, the latter form being, for example, of the general type as a USB serial port but any other serial addressing form is within the scope of the invention. Such alternative embodiment could be used, for example, on superficial brain stimulation or in TENS devices (Transcutaneous Electrical Neural Stimulation)

Another alternative embodiment is the use of devices to move the picafina (or cordum, or TENS) that are not standard electric motors. For example, the picafina (or cordum, or TENS) may be attached to a piezoelectric crystal, which control its position. The persons skilled in the arts of technology are aware that piezoelectric crystals change dimensions with the application of electric fields (that is, voltage) to them. Piezoelectric crystals are in fact widely used in laboratories to adjust position of devices. The total reach of a piezoelectric crystal is small, but it can be built with a ratchet-type device, one that moves the device a small amount, then holds the new position with a ratchet, release the piezoelectric expansion and seat it again in the new position, then expand it again, etc. With such a ratchet Another alternative embodiment is to use a partial motor. An electric motor is composed of two parts, one which creates a magnetic field, another that suffers a force induced by the magnetic field. Energy is fed into the system by electricity which creates the magnetic field, this energy being responsible for the rotation of the motor. The part of the motor that rotates is generally known as the "rotor", while the part that creates the magnetic field is generally known as "stator". It is possible, to save space and battery energy, to have only the stator at the proximal extremity of the picafina, but not the stator. If the need arises to move the picafina, the patient would go to a physician's office, who has the necessary equipment to apply the necessary magnetic field on the rotor at the proximal end of the picafina, therefore rotating it. Looking it from a different point of view, this alternative embodiment uses an external stator. Of course that an external stator, being further away from the rotor, must create a stronger magnetic field, using more energy than the standard motor, which has a stator right around the rotor. But in this case it is a good trade, because a totally self-contained motor would have to use the battery energy, while an external stator would use an external source, say the so-called wall-plug. Such a variation has the advantage of decreasing the size and complexity of the equipment attached to the picafina, while obviating the use of battery energy to effect the motion as well.

In another alternative embodiment, herein called cordum, shown in FIG. 7, the stimulating device is designed to work as a heart pacemaker. Some pacemakers are attached on the outside wall of the heart, other pacemakers are attached on the inner wall of the heart. We will describe here the latter, but our invention is not limited to the position of the electrode being on the inner or outer heart surface, as it will be apparent for the practitioners of the art. Pacemakers that are attached to the inner wall of the heart are inserted into the heart from a generally neck located vein. For this alternative embodiment, the general shape of the distal end of the device is of a short screw or some other form which allows the electrode to become fixed on the heart inner wall, which is made of a non-conductive material as a plastic that is compatible with human tissues, with electrically conductive pads, or electrodes, on its surface, which are connected to an electric energy source (as a battery or a charged capacitor) by appropriate electronic circuits described below. Both the non-conductive structure and the metallic conductive pads have to be made of any of the existing art materials compatible with human tissues. As in prior art, the screw capable of being screwed onto the inner wall of the heart, often onto the inner wall of the ventricule, but can be in other parts too. Current art devices are screwed onto the inner heart wall for mechanical stability, often in the inner ventricular wall, but not necessarily so, other options being used, alone or together with a ventricular pacemaker. In our improved invention, after fixing the screw in the heart, the desired electrical stimulation is send by the connecting wires, as known by the practitioners of the art, to one or more of the electrical stimulating pads or electrodes PADi (i=1, 2, 3, . . . etc.). The choice of pads is made by trial and error by the surgeon, or later by another physician or medically trained personnel, observing on a EKG the effects of applying the electric pulses on a combination of pads. The inventors believe that the choice depends on the particular path of electrical conduction for the particular patient, and for the particular location of the stimulator, but our invention is not bound to any particular theory, but rather on the effects it produces. With pads as shown in FIG. 7, it is possible to apply the pacemaking electrical pulse at a precise depth onto the heart wall, as pads further down are selected, and also at any particular direction, as pads are chosen around the screw, as changing from PAD1 to PAD2, or even more, changing from PAD1 to PAD1 and PAD3 together, or even more, as changing from PAD1 to PAD3, etc. The pads that are energized (that is, the pads that are originating points for a pacemaking pulse), are selected by a digital addressing system which compares an address sent by a controlling unit to an address characteristic of each pad. The comparison is made by a standard digital circuit known as a comparator, well known in the art of digital electronics (reference-_HorowitzAndHill). When a match is found the particular pad becomes an originating point for a pacemaking pulse. To allow for more than one pad at a time, or for more than one pad at different times, said comparators are associated with a combination of pulse stretchers and latches, both being well known circuits in the art of analog and digital electronics. A possible combination may be, for example, that every time that a pad is selected, it stays selected until it is deselected by a pulse described below. Or is can be that in another possible alternative, one a pad is selected, it turns on for a particular delay time, the value of which can also be sent on the communication lines described below, all according to a pre-programmed sequence. The pad addresses and pulse delays are binary digital numbers, as used by the art of digital electronics, and the values may be sent either in parallel or in serial form. The latter may be preferred due to the difficult of passing too many wires in the cable connecting the cordum to the battery/electronics control unit, a serial communication using less wires, perhaps only two wires (bit and return or ground), or four wires (as in a USB-type serial communication), or another small number of wires, depending on the particular type of serial communication is used. This invention is not depending on any particular serial communication, which is part of the old art of digital electronics, but it depends only on the possibility of selecting particular electrode pads, which in turn select the depth and direction of insertion of the pacemaking pulse in the heart wall. The digital (parallel and serial) method is described in other pending patent of some of the authors of this patent (PPA "Method and means to address and make use of multiple electrodes for measurements and electrical stimulation of neurons and other cells including brain and heart" by Chong Il Lee and Sergio Monteiro, application No. 61/340,920 of Mar. 24, 2010, RPA "Method and means for connecting and controlling a large number of contacts for electrical cell stimulation in living organisms" by Chong Il Lee and Sergio Monteiro, application Ser. No. 12/586,763, of Sep. 28, 2009, RPA "Method and means for connecting a large number of electrodes to a measuring device" by Chong Il Lee and Sergio Monteiro, application Ser. No. 12/586,562, of Sep. 24, 2009), which are included as references in their enterity, and also copied in part in this PPA.

Saying the above in different way, alternative description, the innovation of our invention over prior art is the introduction of several relatively small points from where to originate the pacemaking pulses, in stark difference with the prior art, with which the pacemaking pulses have been introduced in the heart over the whole size of the anchoring electrode and over 360 degrees around same. The smaller originating points for the pacemaking points require the use of an addressing system to select one or a plurality of points as originating points for the pacemaking pulses, which can be made using the digital addressing system disclosed in the invention of some of us (PPA "Method and means to address and make use of multiple electrodes for measurements and electrical stimulation of neurons and other cells including brain and heart" by Chong Il Lee and Sergio Monteiro, application No. 61/340, 920 of Mar. 24, 2010, RPA "Method and means for connecting and controlling a large number of contacts for electrical cell stimulation in living organisms" by Chong Il Lee and Sergio Monteiro, application Ser. No. 12/586,763, of Sep. 28, 2009, RPA "Method and means for connecting a large number of electrodes to a measuring device" by Chong Il Lee and Sergio Monteiro, application Ser. No. 12/586,562, of Sep. 24, 2009), which is included in this PPA in their entirety and partly copied as part of this application. The possibility of selecting a smaller surface area as initiating position for the pacemaking pulses allow the medical professional to introduce the pacemaking pulse in the particular depth and on the particular direction that is better suited for the correct propagation of the pacemaking pulse both in timing and phase, thereby creating a better heart beating, which is more similar to the desired one when compared with prior art pacemakers.

For the embodiment we call cordum, the rotating motion can be imparted to the tip of the device either using the same technology as used in current art, or it can be implemented by means of a rotating means at the distal extremity of the device, at or near the heart muscle, where the stimulating implant is located. Such a rotating means may be an electrical motor, but this is not necessarily so. Such a rotating means (motor or otherwise) may be also located at the proximal extremity of the cable, still within the scope of our invention. Such a rotating device and be exactly and only the existing art attachment, in which case the electrode initiation point is only based on the electrode selection, or the rotating device can be with a motor to adjust the positioning after surgery.

then is applied to the heart by the metallic screw, from where it propagates on all 360 degrees directions out of the screw-like cordum. In the variation disclosed by our invention, the cordum is made similarly to the picafina, having a number of contacts on its surface, as seen in FIG. 7, FIG. 11, which are capable of delivering the stimulation at a chosen depth, determined according to the case and according to the patient needs. Also possible is to deliver the stimulation towards one direction only, the degree of directionality depending on the arc determined by each electrode. Both the directionality and the depth are known to be important factors for the pacemaker, yet to this day there exist no pacemaker capable of selecting the depth of stimulation nor the direction of stimulation. The objective of the invention is to mimic as well as possible the natural electric pulse traveling through the heart muscle, which is not nearly close achieved by existing art pacemakers.

FIGS. 8, 8a and 8b display another possible embodiment, in which the motor MOT1 is provided with a sleeve, which rides inside a slot on the support structure, which then allows the motor to move in-and-out of the brain as its axis rotates, while preventing the whole motor from rotating, that is rotating around a fixed picafina.

FIG. 8c displays other possible embodiments for adjusting the position of the electrodes, both axially (along the picafina's long dimension, or z-axis) and rotationally (along the theta or angular dimension). In this embodiment the motor is fixed and the advancement of the picafina is absorbed by a longer connecting axle CON-AXLE, which is long enough to stay in contact with the matching slot on the motor, while moting along its z-dimension.

FIG. 9 displays a solution to the problem of the relative position of the picafina with respect to the skull. The surgeon attempts to insert the picafina perpendicularly to the skull outer surface, but this is seldom accomplished perfectly, a small angle usually being necessary to adjust to the peculiar position of the area of interest, which is different from person to person, from patient to patient. In old art the picafina is cemented on a plate which is screwed on the skull, but our invention uses an intermediate motor, or motors. This necessitates the introduction of an angle adjusting wedge ANG1, which seats an angled picafina and motor on a support that may be not at 90 degrees to the picafina z-axis. The angle adjusting wedge is selected at the end of surgery, by trial and error, or measuring the angle between the picafina z-axis and the skull's locally flat surface (locally flat is here used in the mathematical sense, which is an osculating plane). In that case the picafina is first inserted in place using existing art devices and techniques, then SUPP1-SIDE (see FIG. 10) is screwed around it as deep as needed, then a longer measuring device (not shown) is inserted onto the hexagonal CON-AXLE, which protrudes beyond the skull, from which the angle can be measured and the appropriate angle adjusting wedge ANG1 is chosen, then the motor MOT1 is inserted in place, its distal axle matching the proximal connecting axle CON-AXLE of the picafina, then the wedge ANG1 is inserted and screwed on the motor, then finally the closing plate is screwed on the wedge ANG1 and on the skull, after which the whole device is fixed.

Note that our picafina allows for adjustment both of necessary angle of insertion of the stimulation, as shown in FIG. 5a and FIG. 5b, and also the necessary optimal depth of the electrode (or electrodes), to be at the center of the region of interest, as shown in FIG. 12a and FIG. 12b.

Conclusion, Ramifications, and Scope of Invention

Thus the reader will see that the device of my invention, whether of the picafina (or brain) style, or of the cordum (or heart) style, or of the TENS (or skin) style, provides a highly reliable support for the electrical stimulation, in such a way that the point of electrical stimulation can be modified as needed, both along the translational and along the rotational dimensions.

While my above description contains many specificities, these should not be construed as limitations on the scope of the invention, but rather as an exemplification of one preferred embodiment thereof and a few exemplary variations. Many other variations are possible. For example instead of a long, circularly shaped device, a flat support, similar to a sheet, can also be used for brain cortex stimulation, for heart stimulation, etc.

Accordingly, the scope of the invention should be determined not by the embodiment(s) illustrated, but by the appended claims and their legal equivalents.

In order to avoid obscuring the features of the present invention, the description is provided with reference to single ended implementations. The extension of the approaches to differential circuits will be apparent to one skilled in the relevant arts by reading the disclosure provided herein, and such implementations are contemplated to be covered by various aspects of the present invention.

One skilled in the relevant art, however, will readily recognize that the invention can be practiced without one or more of the specific details, or with other methods, etc. In other instances, well known structures or operations are not shown in detail to avoid obscuring the features of the invention.

SEQUENCE LISTING

Not applicable

DEFINITIONS

References

INV1: (PPA) "Method and means to address and make use of multiple electrodes for measurements and electrical stimulation of neurons and other cells including brain and heart" by Chong Il Lee and Sergio Monteiro, application No. 61/340,920 of Mar. 24, 2010, INV2: (RPA) "Method and means for connecting and controlling a large number of contacts for electrical cell stimulation in living organisms" by Chong Il Lee and Sergio Monteiro, application Ser. No. 12/586,763, of Sep. 28, 2009, INV3: (RPA) "Method and means for connecting a large number of electrodes to a measuring device" by Chong Il Lee and Sergio Monteiro, application Ser. No. 12/586,562, of Sep. 24, 2009)

Eric Kandel (Kandel (2000)) gives a good overview of the current state of the art from the academic point-of-view Paul Horowitz and Winfield Hill "The Art of Electronics", $1^{st}$ and $2^{nd}$ eds, Cambridge University Press, Boston, Mass. Good for non-specialist (though technically trained) persons, that is, persons capable of think about electronic circuits, as a physicist or chemist or an electronics technician, but not necessarily EE.

We claim:

1. A method of adjusting the positioning of an electrical stimulating device configured to be implanted in an animal comprising:
   providing a first supporting structure (SUPP1) configured to be attached to the animal;
   providing an electrode supporting structure with a proximal extremity, a distal extremity, a surface and an inner lumen;
   providing a plurality of electrodes at the surface of the distal extremity of the electrode supporting structure;
   providing a connecting structure attached to the SUPP1 which is configured to
   support the electrode supporting structure;
      the connecting structure comprises a translation structure for engaging and supporting the electrode support structure, and for providing motion to the electrode supporting structure, in such a way that the plurality of electrodes at the surface of the electrode supporting structure adopt new positions with respect to the intended target tissue of the animal;
      the translation structure comprises a central aperture configured to accept insertion of the electrode support structure, wherein the aperture includes tapped screw threads for engaging corresponding tapped screw threads located on the surface of the proximal extremity of the electrode support structure, and facilitating advancement of the electrode support structure to the target tissue due to the motion provided by the connecting structure.

2. The method of claim 1 wherein the motion provided by the connecting structure attached to the SUPP1 provides rotating motion to the electrode supporting structure in such a way that the plurality of electrodes at the surface of the electrode supporting structure adopt new positions with respect to the intended target tissue of the animal which are displaced by rotations with respect to the initial position.

3. The method of claim 1 wherein the motion provided by the connecting structure attached to
   the SUPP1 provides a linear translating motion to the electrode supporting structure in such a way that the plurality of electrodes at the surface of the electrode supporting structure adopt new positions with respect to the intended target tissue of the animal which are displaced by linear translations with respect to the initial position.

4. The method of claim 1 wherein the connecting structure comprises an electric motor for providing the motion of the electrode supporting structure.

5. The method of claim 2 wherein the rotating motion is configured to rotate the electrodes by a maximum angle larger than an angle between two electrodes.

6. The method of claim 3 wherein the translating motion is configured to move the electrodes by a maximum distance larger than a distance between the electrodes along the direction of motion.

7. An electrical stimulation apparatus, comprising; a first supporting structure (SUPP1) configured to provide fixed attachment to an animal; an electrode supporting structure with a proximal extremity, a distal extremity, an inner lumen and a surface;
   a plurality of electrodes located at the surface of the distal extremity of the electrode supporting structure; and
   means for moving the electrode supporting structure with respect to the SUPP1 when attached to the animal,
      the means for moving the electrode supporting structure comprises translation means for engaging and supporting the electrode support structure, and for providing motion to the electrode supporting structure, in such a way that the plurality of electrodes at the surface of the distal extremity of the electrode supporting structure adopt new positions with respect to the intended target tissue of the animal;
      the translation means comprising a central aperture configured to accept insertion of the electrode support structure, wherein the aperture includes tapped screw threads for engaging corresponding tapped screw threads located on the surface of the proximal extremity of the electrode support structure, and facilitating advancement of the electrode support structure to the target tissue due to the motion provided by the connecting structure.

8. The electrical stimulation apparatus of claim 7 where the means for moving the electrode supporting structure with respect to the SUPP1 is configured for rotating the electrode supporting structure,
   whereby the plurality of electrodes at the surface of the distal extremity of the electrode supporting structure assume
   different positions that differ from the original position by rotation of the electrode supporting structure with respect to the intended target tissue of the animal.

9. The electrical stimulation apparatus of claim 7 where the means for moving the electrode supporting structure with respect to the SUPP1 is configured for linearly translating the electrode supporting structure,
   whereby the plurality of electrodes at the surface of the distal extremity of the electrode supporting structure assume different positions that differ from the original position by linear translation with respect to the intended target tissue of the animal.

10. The electrical stimulation apparatus of claim 7 where the means for moving the electrode supporting structure with respect to the SUPP1 is an electric motor.

11. The electrical stimulation apparatus of claim 8 where the means for rotating the electrode supporting structure with respect to the SUPP1 is configured to cause a maximum rotation larger than an angular separation between the electrodes along the direction of rotation.

12. The electrical stimulation apparatus of claim 9 where the means for translating the electrode supporting structure with respect to the SUPP1 is configured to cause a maximum translation larger than a distance between the electrodes on the surface of the electrode supporting structure.

13. An electronics control unit for aiding in the positioning of an electrode support structure, in accordance with the method of claim 1, wherein the electronics control unit provides an electrical control signal to an electric motor configured to provide the motion that moves the electrode support structure with respect to the first supporting structure (SUPP1).

14. The electronics control unit of claim 13, is configured to control the electric motor to provide rotational motion to the electrode supporting structure, wherein electrodes located at a distal extremity of a surface of the electrode supporting structure are rotated by a specified angle.

15. The electronics control unit of claim 13, is configured to control the electric motor to provide linear translational motion to the electrode supporting structure, wherein electrodes located at a distal extremity of a surface of the electrode supporting structure are linearly translated by a specified distance.

* * * * *